(12) United States Patent
Frey et al.

(10) Patent No.: US 11,000,233 B2
(45) Date of Patent: May 11, 2021

(54) MEDICAL SENSOR ASSEMBLY

(71) Applicant: ROCHE DIABETES CARE, INC., Indianapolis, IN (US)

(72) Inventors: Stephan-Michael Frey, Pfungstadt (DE); Oliver Kube, Worms (DE); Helmut Walter, Heppenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 554 days.

(21) Appl. No.: 15/412,916

(22) Filed: Jan. 23, 2017

(65) Prior Publication Data
US 2017/0128011 A1 May 11, 2017

Related U.S. Application Data

(63) Continuation of application No. PCT/EP2015/067222, filed on Jul. 28, 2015.

(30) Foreign Application Priority Data

Jul. 28, 2014 (EP) .................................... 14178704

(51) Int. Cl.
*A61B 5/145* (2006.01)
*A61B 5/1473* (2006.01)
(Continued)

(52) U.S. Cl.
CPC .......... *A61B 5/6849* (2013.01); *A61B 5/1473* (2013.01); *A61B 5/14532* (2013.01);
(Continued)

(58) Field of Classification Search
CPC ..... A61B 5/684; A61B 5/685; A61B 5/14532; A61B 5/6832; A61B 5/1473; A61B 5/14865; A61B 5/6833; A61M 25/02
See application file for complete search history.

(56) References Cited

U.S. PATENT DOCUMENTS 4,324,237 A * 4/1982 Buttaravoli ........... A61M 25/02
602/54
4,969,880 A * 11/1990 Zamierowski .... A61F 13/00068
604/180
(Continued)

FOREIGN PATENT DOCUMENTS

DE        3924599 A1 *  1/1991  ............ A61M 25/02
EP     0 678 308 A1    10/1995
(Continued)

OTHER PUBLICATIONS

EPO machine translation of DE3924599. Retrieved on Jul. 29, 2019. (Year: 2019).*

(Continued)

*Primary Examiner* — Matthew Kremer
*Assistant Examiner* — Samuel C Kim
(74) *Attorney, Agent, or Firm* — Bose McKinney & Evans LLP

(57) ABSTRACT

A medical sensor assembly comprises a flexible plaster adapted for adhesion on the skin of a patient and a sensor configured for transdermal measuring a physiological parameter, wherein the sensor has a measuring part insertable into the skin and a contact part for providing a signal connection to a measuring unit. It is proposed that the plaster has a flap which is adhered to an intermediate section of the sensor between the measuring part and the contact part.

20 Claims, 3 Drawing Sheets

(51) Int. Cl.
*A61B 5/1486* (2006.01)
*A61B 5/00* (2006.01)
*A61M 25/02* (2006.01)

(52) U.S. Cl.
CPC ........ *A61B 5/14865* (2013.01); *A61B 5/6832* (2013.01); *A61B 5/6833* (2013.01); *A61M 25/02* (2013.01); *A61M 2025/028* (2013.01); *A61M 2025/0246* (2013.01); *A61M 2025/0266* (2013.01)

(56) References Cited

U.S. PATENT DOCUMENTS

| | | | | |
|---|---|---|---|---|
| 5,221,265 | A * | 6/1993 | List | A61M 25/02 128/DIG. 26 |
| 5,390,671 | A * | 2/1995 | Lord | A61B 5/14865 204/403.01 |
| 5,586,553 | A * | 12/1996 | Halili | A61B 5/14532 600/316 |
| 6,134,461 | A * | 10/2000 | Say | A61B 5/14532 600/345 |
| 6,175,752 | B1 * | 1/2001 | Say | A61B 5/14532 128/903 |
| 6,936,006 | B2 * | 8/2005 | Sabra | A61B 5/14532 600/300 |
| 9,795,327 | B2 * | 10/2017 | Shoshihara | A61B 5/14532 |
| 2002/0099282 | A1 * | 7/2002 | Knobbe | A61B 5/0002 600/365 |
| 2002/0198444 | A1 * | 12/2002 | Uchigaki | G01N 33/4875 600/345 |
| 2003/0023317 | A1 * | 1/2003 | Brauker | A61B 5/076 623/23.76 |
| 2005/0131305 | A1 * | 6/2005 | Danielson | A61B 5/14532 600/481 |
| 2008/0135408 | A1 * | 6/2008 | Sjolander | A61B 5/1468 204/403.01 |
| 2010/0063372 | A1 * | 3/2010 | Potts | A61B 5/14521 600/346 |
| 2011/0021889 | A1 | 1/2011 | Hoss et al. | |
| 2012/0035447 | A1 | 2/2012 | Frey et al. | |
| 2015/0126842 | A1 * | 5/2015 | Padalino | A61B 5/0492 600/377 |

FOREIGN PATENT DOCUMENTS

| | | |
|---|---|---|
| EP | 1 698 368 A1 | 9/2006 |
| EP | 2 415 395 A1 | 2/2012 |
| WO | WO 97/21459 A1 | 6/1997 |
| WO | WO 2013/130711 A1 | 9/2013 |

OTHER PUBLICATIONS

Drew, J. H., Padoms, K., & Clabburn, S. L. (1986). Endotracheal Tube Management in Newborn Infants with Hyaline Membrane Disease. Australian Journal of Physiotherapy, 32(1), 3-5. doi: 10.1016/s0004-9514(14)60637-1 (Year: 1986).*

* cited by examiner

MEDICAL SENSOR ASSEMBLY

RELATED APPLICATIONS

This application is a continuation PCT/EP2015/067222, filed Jul. 28, 2015, which claims priority to EP 14 178 704.4, filed Jul. 28, 2014, both of which are hereby incorporated herein by reference in their entireties.

BACKGROUND

The invention relates to a medical sensor assembly comprising a flexible plaster adapted for adhesion on the skin of a patient and a sensor configured for transdermal measuring a physiological parameter, wherein the sensor has a measuring part insertable into the skin and a contact part for providing a signal connection to a measuring unit.

In the area of medical technology in the field of continuous glucose monitoring (CGM), a similar assembly is proposed in U.S. Publication No. 2012/0035447. This document discloses an implantable sensor device in connection with a rigid base plate, which is part of a disposable or body-mount fixed to the body by means of a plaster. In this connection a wearing period of at least several days is intended. Thus, inadvertently detaching the carrier plaster from the body should be avoided.

SUMMARY

The present disclosure further improves the known devices and achieves an improved efficiency for reliable, long-term use and at the same time uncomplicated handling.

This disclosure is based on the idea of providing the sensor in fixed connection to the plaster (also referred to herein as "patch"). Correspondingly, it is proposed according to this disclosure that the plaster has a flap which is adhered to an intermediate section of the sensor between the measuring part and the contact part. These measures guarantee that the sensor is securely and comfortably attached to the patient's skin, specifically in the implantation area where movement could cause erroneous measuring results. Moreover, due to the direct attachment to a flexible structure, a better conformation to the local body shape at the application site is achieved, while a rigid base plate can be avoided. Thus, the possible wearing time is increased, and the risk of detachment due to shearing forces is reduced. Furthermore, the design of the assembly is simpler and less complicated to produce.

One embodiment provides that the flap is formed as a partially cut-out or punched segment of the plaster, such that an opening is provided in the plaster when the flap is folded up for the passage of the intermediate section of the sensor. Thus, a reach-through opening and a connecting element is provided for the sensor with a simple measure at the same time.

In a specific embodiment, the flap is delimited by a preferably U- or C-shaped cutting line so that a material bridge remains intact to bendably connect the flap to the remaining plaster.

In order to provide an easy connection it is advantageous when the bottom side of the plaster facing the skin is coated with a pressure-sensitive adhesive coating and the flap is fixedly connected to the intermediate section of the sensor by means of this adhesive coating. It is also conceivable that the flap is fixed to the sensor by different means, e.g., a structural adhesive which is applied in the joining zone.

For further use it is advantageous when a hollow inserter cannula is provided in which the sensor at least with its measuring part is located for insertion into the skin, wherein the inserter cannula has a longitudinal slit at least along a distal section for the reach-through of the flap. In this way, it is also possible to prefabricate the combined inserter/sensor assembly while the sensor is already fixedly connected to the plaster.

One embodiment provides that the measuring part of the sensor is formed by a flexible flat substrate provided with electrode pads or conducting paths thereon. Thus, the sensor can be implanted in the skin for long-term wear without skin irritation due to rigid parts. Moreover, the flap can be easily connected to a flat side of the substrate, thus maintaining a secure connection even with a small adherent area.

A further improvement provides that the intermediate section of the sensor is formed by a material strip provided with electrically conducting paths, such that the measuring signals can be routed to a body-mounted contact part. In this context, it is also advantageous when the contact part of the sensor is arranged preferably in direct abutment on the upper side of the plaster facing away from the skin. Then, a rigid base with laborious arrangement for sensor fixation can be omitted.

In another embodiment there is provided a signal transmitter which can be connected to the contact part of the sensor, wherein the signal transmitter is directly fixed to the plaster. Again, this allows a more flexible design, also in case the transmitter is reused.

Another improvement also with respect to simplified handling provides that the signal transmitter has a socket to receive the contact part of the sensor by means of transverse pressing against the plaster or by lateral insertion.

Another particularly advantageous embodiment provides that the plaster below its upper side defines at least one channel leading from the sensor to the margin of the plaster for conducting blood emerging from a skin wound. In this way, blood can be discharged below the upper surface of the plaster, thus avoiding impairment of the contact part of the sensor.

Advantageously, the channel is formed by a gap between segments or layers of the plaster preferably as a capillary gap.

In order to counteract problems due to bleeding from the skin wound, e.g., detachment of the wetted plaster or disturbance of the measurements, it is advantageous when a performance indicator is integrated in the plaster to signal excessive blood load or wear to the user preferably by a color change.

For further handling improvement it is advantageous when an inserter for moving the inserter needle into the skin is provided, wherein the plaster affixed to the sensor by means of the flap, and wherein the inserter is supported on the upper side of the plaster preferably by an adherend surface.

This disclosure also concerns a use wherein the sensor is a glucose sensor adapted for continuous glucose monitoring.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

Figure 1:
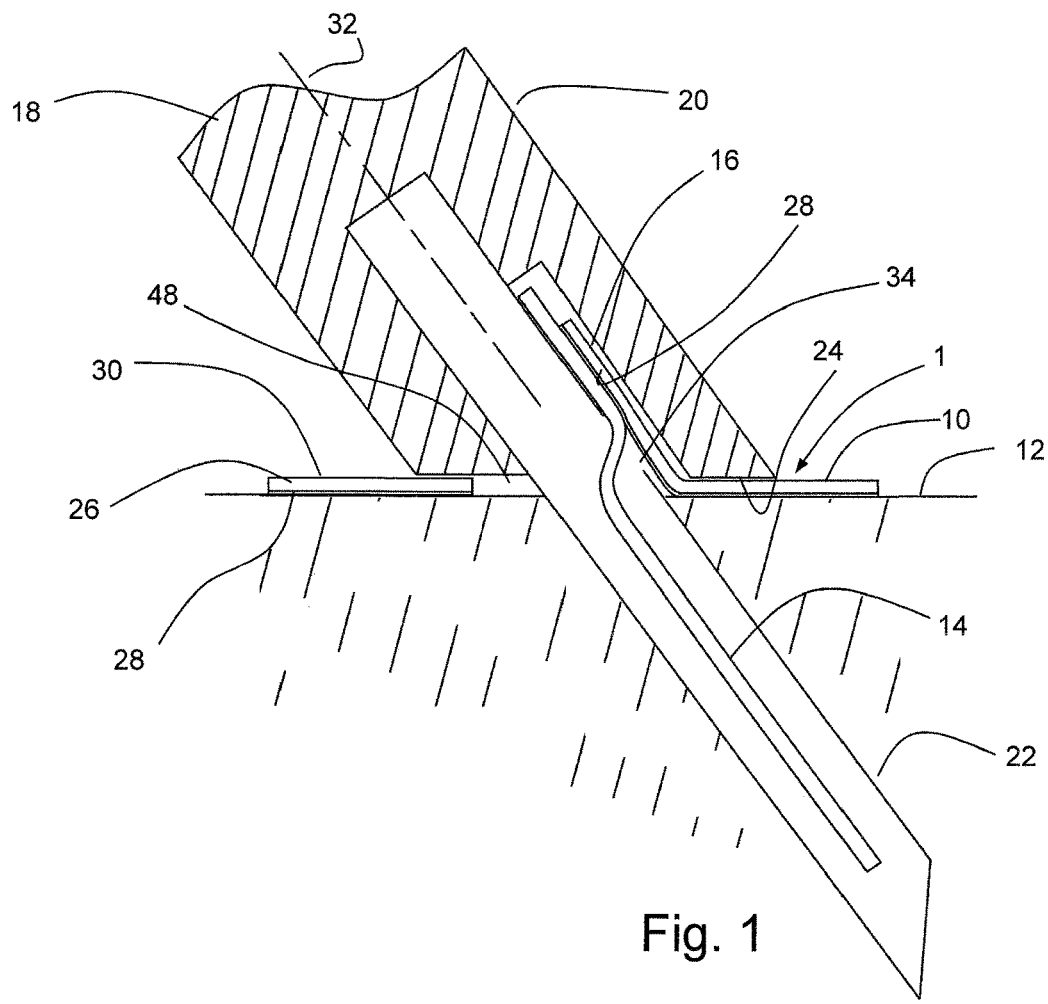
FIG. 1 is a sectional view of a medical sensor assembly connected to a partially illustrated inserter provided for transdermal insertion.

The embodiments described below are not intended to be exhaustive or to limit the invention to the precise forms disclosed in the following description. Rather, the embodiments are chosen and described so that others skilled in the art may appreciate and understand the principles and practices of this disclosure.

Referring to the drawings, a medical sensor assembly 1 worn on the body for long-term diagnostic applications comprises a flexible patch or plaster 10 adapted for adhesion on the skin 12 of a patient and a sensor 14 configured for transdermal measuring a physiological parameter, wherein the plaster 10 has a flap 16 which is permanently adhered to the sensor 14.

In an initial condition as illustrated in FIG. 1, an inserter 18 is provided in connection with the sensor assembly 1 in order to facilitate the implantation of the sensor 14 into the skin 12. The inserter 18 comprises a support 20 and a hollow cannula 22 received with its proximal section in the support 20. The support 20 has an end face 24 which adheres to an upper surface of the plaster 10. The flexible sensor 14 extends into the distal part of the rigid cannula 22 such that skin penetration is possible. This can be handled manually by means of a stamp (not shown) connected to the support 20.

The plaster 10 comprises a carrier layer 26 and a pressure-sensitive adhesive coating 28 on its side facing the skin 12. A lateral overlap 30 of the plaster 10 over the support end face 24 allows additional manual fixation on the skin 12 before removal of the inserter 18. The adherency of the end face 24, which can be coated with a transfer adhesive, is less than that of the adhesive coating 28 in order to avoid detaching of the plaster 10 when withdrawing the inserter 18. The inserter 18 can be configured to have an insertion angle between 45° and 90° of the lancing axis 32 with respect to the surface of the skin 12.

Figure 2:
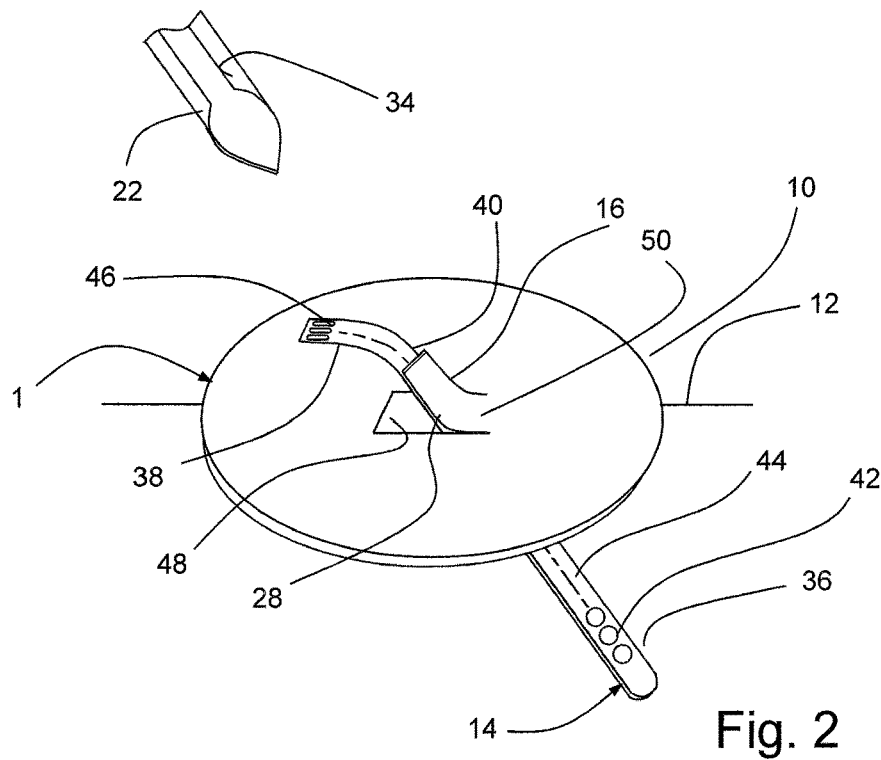
FIG. 2 is a perspective view of the implanted sensor assembly with the inserter being removed.

As apparent from FIG. 2, the inserter cannula 22 has a longitudinal slit 34 formed at least along a distal section. This allows a reach-through of the sensor 14 in connection with the flap 16 in the condition as supplied and when retracting the cannula 22.

As further illustrated in FIG. 2, the sensor 14 consists of a flexible strip which has a distal measuring part 36, a proximal contact part 38 and an intermediate section 40 therebetween. The measuring part 36 is provided with electrode pads 42 for electrochemical detection of a physiological parameter. Specifically, the electrode pads 42 can be configured for continuous glucose measuring in the interstitial fluid of the skin 12. Electrically conducting paths 44 lead from the pads 42 through the intermediate section 40 to leads 46 in the contact part 38.

The flap 16 is formed as a U-shaped punched segment of the plaster 10, such that an opening 48 is provided in the plaster for the passage of the sensor 14 and a material bridge 50 remains to bendably connect the flap 16 to the remaining area of the plaster 10. At the same time, the flap 16 is fixedly connected to the intermediate section 40 of the sensor 14 by means of the adhesive coating 28.

Figure 3:
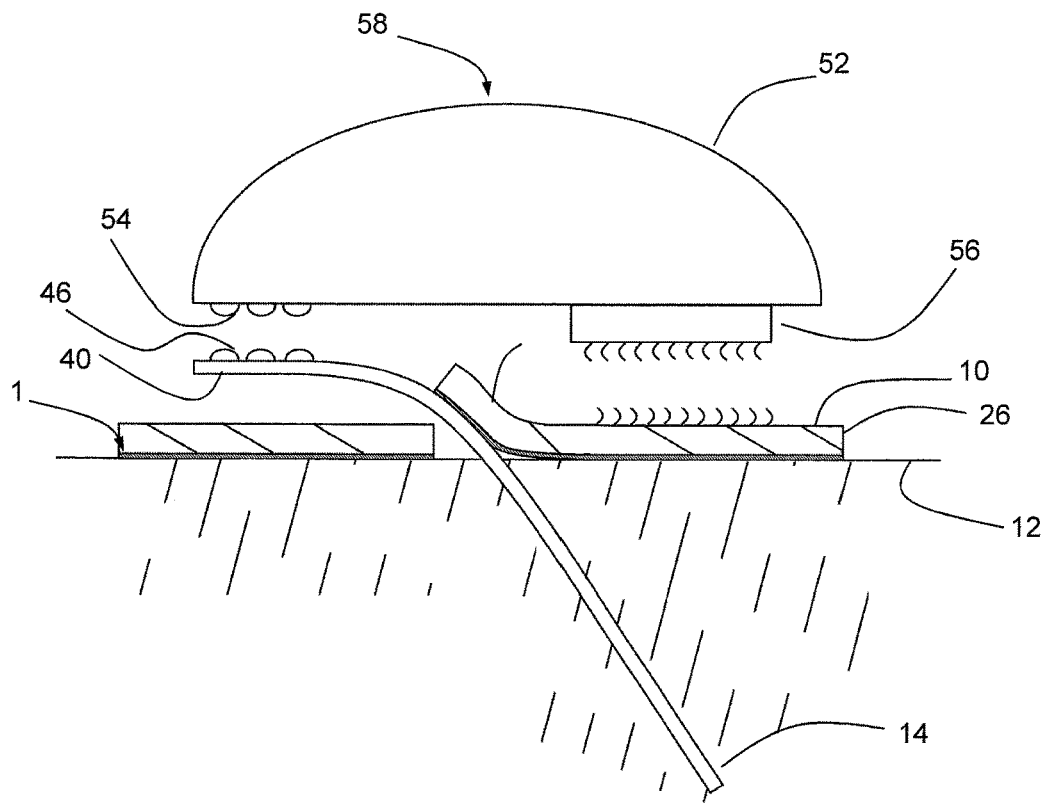
FIG. 3 is a sectional view of the assembly of FIG. 2 when mounting a signal transmitter.

FIG. 3 illustrates the sensor arrangement in a further assembly condition comprising a signal transmitter 52 configured to transmit measuring signals from the sensor 14 to a measuring or controller unit (not shown). For this purpose, the transmitter 52 has a socket 54 which can be engaged with the leads 46 of the contact part 40. The signal transmitter 52 is directly fixed to the carrier layer 26 of the plaster 10 by means of a hook-and-loop tape 56 or other quick fasteners. As indicated by arrow 58, the joining movement of the transmitter 52 is transverse to the plaster 10, such that in the connected state the contact 40 of the sensor 14 is arranged in direct abutment on the carrier layer 26 facing away from the skin 12.

Figure 4:
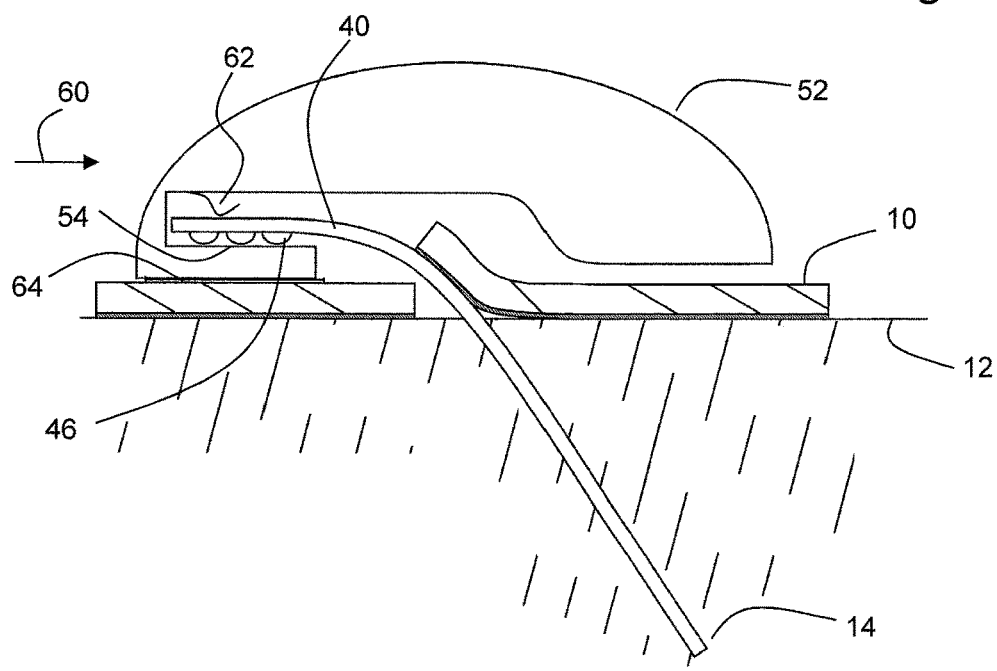
FIG. 4 is a further embodiment in a view similar to FIG. 3.

FIG. 4 shows an alternate arrangement of the transmitter 52 wherein the socket 54 is construed for a lateral insertion of the contact part 40 by a joining movement of the transmitter 52 in direction of arrow 60. Then, the electrical contact between the leads 46 and the socket 54 is supported by a pre-loaded spring 62. Again, the transmitter 52 is directly fixed on the plaster 10, e.g., by adhesive connection 64, thus making an additional rigid base plate superfluous.

Figure 5:
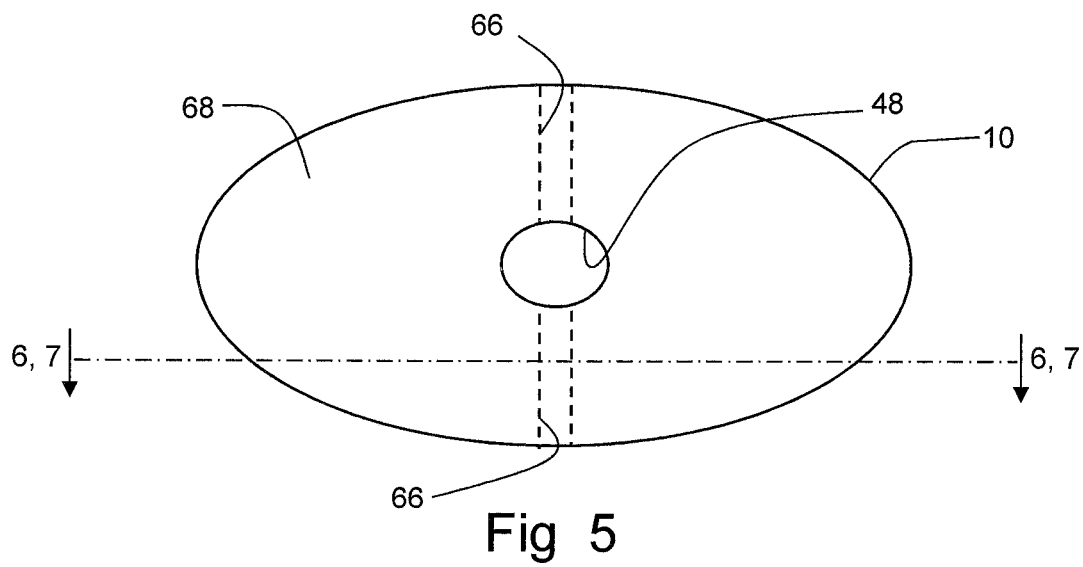
FIG. 5 is a top view of a plaster of the sensor assembly provided with a blood discharge channel.

FIG. 5 shows an embodiment in which the plaster 10 is provided with radial blood discharge channels 66 leading from the central opening 48 to the outer margin. The channels 66 are provided below the upper surface 68 of the plaster 10 and conduct blood which may emerge from the skin wound created with the cannula 22. Conveniently, the channels 66 are designed as capillary gaps or slits for self-acting fluid transport. In order to facilitate the blood discharge, the channels 66 can be provided with a hydrophilic coating.

Figure 6:
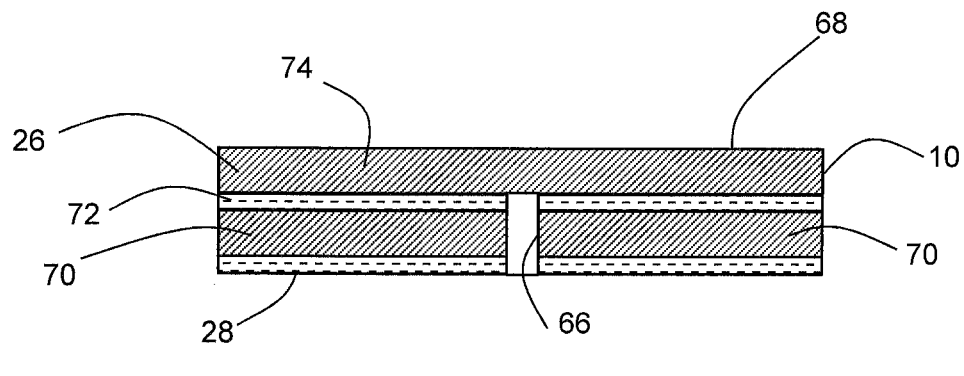
FIGS. 6 and 7 are sectional views of alternate discharge channel embodiments of the plaster along line 6, 7 of FIG. 5.
Figure 7:
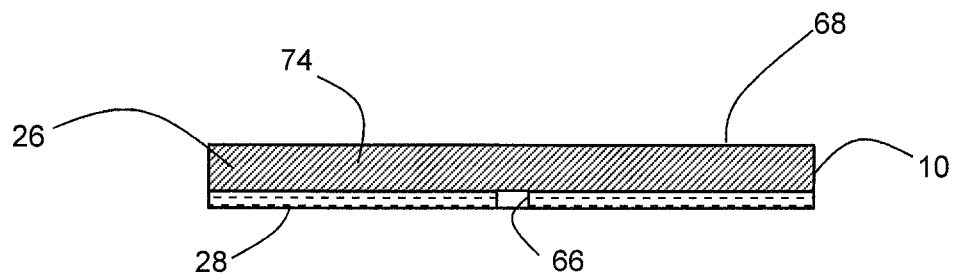

As illustrated in FIG. 6, the plaster 10 can be provided with an additional intermediate layer 70 which is divided in two segments or halves to define the channel 66. In this case, a transfer adhesive 72 provides the connection to the carrier layer 26. Alternatively, the channel 66 can be directly formed in the adhesive coating 28 facing the skin 12, as apparent from FIG. 7. In both cases, the carrier layer 26 can be loaded with an indicator substance 74 to signalize unstopped bleeding or excessive blood load to the user, e.g., by a color change.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A medical sensor assembly, comprising:
 a flexible patch configured for adhesion to skin of a patient;
 a sensor configured for transdermal measuring of a physiological parameter, the sensor comprising (i) a measuring part insertable into the skin and formed as a flexible flat substrate with electrode pads or conducting paths thereon, (ii) a contact part configured for providing a signal connection to a signal transmitter, and (iii) an intermediate section between the measuring part and the contact part;

a flap formed as a partially cut-out or punched segment of the patch, the cut-out or punched segment forming an opening in the patch for passage of the sensor, the flap having a section with a surface that adheres to a side of the sensor in the intermediate section of the sensor; and a hollow inserter cannula in which the sensor at least with its measuring part is positioned for insertion into the skin, wherein the cannula is retractable from the sensor and the patch while the sensor remains adhered to the flap.

2. Medical sensor assembly according to claim 1, wherein the flap is delimited by a U- or C-shaped cutting line so that a material bridge remains intact to bendably connect the flap to the remainder of the patch.

3. Medical sensor assembly according to claim 1, wherein a bottom side of the patch that is configured to face the skin is coated with a pressure-sensitive adhesive and the flap is fixedly connected to the intermediate section by means of the pressure-sensitive adhesive.

4. Medical sensor assembly according to claim 1, wherein the inserter cannula has a longitudinal slit at least along a distal section for reach-through of the flap and/or sensor.

5. Medical sensor assembly according to claim 1, wherein the intermediate section of the sensor is formed of a material strip having electrically conducting paths.

6. Medical sensor assembly according to claim 1, wherein the contact part of the sensor is arranged in direct abutment on an upper side of the patch configured to face away from the skin.

7. Medical sensor assembly according to claim 1, further comprising the signal transmitter, wherein the signal transmitter is directly fixed to the patch.

8. Medical sensor assembly according to claim 7, wherein the signal transmitter has a socket configured to receive the contact part of the sensor by transverse pressing against the patch or by lateral insertion.

9. Medical sensor assembly according to claim 1, wherein the patch defines at least one channel leading from the sensor to the margin of the patch configured for conducting blood emerging from a skin wound.

10. Medical sensor assembly according to claim 9, wherein the channel is formed by a gap between segments or layers of the patch.

11. Medical sensor assembly according to claim 10, wherein the channel comprises a capillary gap.

12. Medical sensor assembly according to claim 1, further comprising a performance indicator integrated in the patch to signal blood load or wear to the user.

13. Medical sensor assembly according to claim 1, further comprising an inserter configured for moving the inserter cannula into the skin, wherein the inserter is supported on an upper side of the patch by an adherend surface.

14. Medical sensor assembly according to claim 1, wherein the sensor comprises a glucose sensor adapted for continuous glucose monitoring.

15. A method of inserting a transdermal sensor into skin of a patient, comprising:
providing a flexible patch;
providing a sensor configured for transdermal measuring of a physiological parameter;
cutting out or punching out a segment of the patch to form a flap and an opening in the patch for passage of the sensor;
inserting the sensor into the opening;
adhering a side of the sensor to a side of the flap, whereby the sensor is adhered to the patch;
using an inserter cannula in which the sensor is at least partially positioned to insert the sensor into the skin of the patient;
adhering the patch to the skin of the patient; and
retracting the cannula from the sensor and the patch while the sensor remains adhered to the flap.

16. The method of claim 15, wherein the step of adhering the sensor to the flap takes place before the step of inserting the sensor into the skin of the patient.

17. The method of claim 15, wherein the step of adhering the sensor to the flap comprises adhering an intermediate portion of the sensor to the flap.

18. The method of claim 15, further comprising connecting a contact part of the sensor to a signal transmitter that is directly fixed to the patch.

19. The method of claim 18, further comprising connecting a socket of the transmitter with the contact part of the sensor by transverse pressing against the patch or by lateral insertion.

20. A medical sensor assembly, comprising:
a flexible patch configured for adhesion to skin of a patient;
a sensor configured for transdermal measuring of a physiological parameter, the sensor comprising (i) a measuring part insertable into the skin and formed as a flexible flat substrate with electrode pads or conducting paths thereon, (ii) a contact part configured for providing a signal connection to a signal transmitter, and (iii) an intermediate section between the measuring part and the contact part; and
a flap formed as a partially cut-out or punched segment of the patch, the cut-out or punched segment forming an opening in the patch for passage of the sensor, the opening having a closed periphery and the flap being adhered to a flat side of the sensor in the intermediate section of the sensor.

* * * * *